(12) United States Patent
Kuenen et al.

(10) Patent No.: US 12,097,166 B2
(45) Date of Patent: Sep. 24, 2024

(54) APPARATUS FOR USE IN MEASURING BLOOD PRESSURE

(71) Applicant: KONINKLIJKE PHILIPS N.V., Eindhoven (NL)

(72) Inventors: Maarten Petrus Joseph Kuenen, Veldhoven (NL); Ralph Wilhelm Christianus Gemma Rosa Wijshoff, Munstergeleen (NL); Jens Muehlsteff, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 626 days.

(21) Appl. No.: 17/430,220

(22) PCT Filed: Feb. 5, 2020

(86) PCT No.: PCT/EP2020/052806
§ 371 (c)(1),
(2) Date: Aug. 11, 2021

(87) PCT Pub. No.: WO2020/164981
PCT Pub. Date: Aug. 20, 2020

(65) Prior Publication Data
US 2022/0160579 A1    May 26, 2022

(30) Foreign Application Priority Data
Feb. 12, 2019    (EP) .................................... 19156730

(51) Int. Cl.
*A61H 31/00*    (2006.01)
*A61B 5/00*    (2006.01)
*A61B 5/022*    (2006.01)

(52) U.S. Cl.
CPC ....... *A61H 31/005* (2013.01); *A61B 5/02225* (2013.01); *A61B 5/4836* (2013.01);
(Continued)

(58) Field of Classification Search
CPC .. A61H 31/005; A61B 5/02225; A61B 5/4836
See application file for complete search history.

(56) References Cited

U.S. PATENT DOCUMENTS

| | | | |
|---|---|---|---|
| 4,461,266 A | 7/1984 | Hood, Jr. et al. | |
| 5,606,977 A | 3/1997 | Ramsey | |

(Continued)

FOREIGN PATENT DOCUMENTS

| | | | |
|---|---|---|---|
| EP | 1127538 A1 | 8/2001 | |
| WO | 2016030232 A1 | 3/2016 | |

(Continued)

OTHER PUBLICATIONS

International Search Report and Written Opinion, International Application No. PCT/EP2020/052806, Mailed on May 15, 2020.

(Continued)

*Primary Examiner* — Eric F Winakur
*Assistant Examiner* — Jaimie Annette McKeel

(57) ABSTRACT

There is provided an apparatus (12) for use in measuring blood pressure. The apparatus (12) comprises a processor (102) configured to acquire a signal indicative of pressure oscillations detected inside a cuff inflated to pressurize a measurement site of a subject undergoing cardiopulmonary resuscitation. The pressure oscillations detected inside the cuff are indicative of a pulse of the subject. The processor (102) is also configured to trigger a blood pressure measurement for the subject based on the pressure oscillations detected inside the cuff.

15 Claims, 10 Drawing Sheets

(52) U.S. Cl.
CPC .. *A61B 2505/01* (2013.01); *A61H 2201/5043* (2013.01); *A61H 2201/5071* (2013.01); *A61H 2230/305* (2013.01)

(56) References Cited

U.S. PATENT DOCUMENTS

| | | | |
|---|---|---|---|
| 2004/0186386 | A1 | 9/2004 | Kolluri et al. |
| 2008/0305464 | A1 | 12/2008 | Lynn |
| 2010/0094140 | A1 | 4/2010 | Pranevicius |
| 2013/0289421 | A1 | 10/2013 | Jarrell et al. |
| 2014/0135634 | A1 | 5/2014 | Pranevicius |
| 2014/0309541 | A1 | 10/2014 | Yamashita et al. |
| 2016/0270673 | A1 | 9/2016 | Aelen et al. |
| 2017/0281015 | A1 | 10/2017 | Tupin |

FOREIGN PATENT DOCUMENTS

| | | |
|---|---|---|
| WO | 2017129495 A1 | 8/2017 |
| WO | 2018064217 A1 | 4/2018 |

OTHER PUBLICATIONS

Barbe, K. et al., "Analyzing the Windkessel Model as a Potential Candidate for Correcting Oscillometric Blood-Pressure Measurements", IEEE Transactions On Instrumentation and Measurement, IEEE Service 30 Center, Piscataway, NJ, US, vol. 61, No. 2, Feb. 1, 2012, pp. 411-418.

T. Tolonen and M. Karjalainen: A computationally efficient multi pitch analysis model. IEEE Trans. on Speech and Audio Processing, 8(6):708-716, 2000.

J. P. Nolan, "High-quality cardiopulmonary resuscitation," Curr. Opin. Crit. Care, vol. 20, No. 00, pp. 1-7, 2014.

B. Eberle, W. F. Dick, T. Schneider, G. Wisser, S. Doetsch, and I. Tzanova, "Checking the carotid pulse check: diagnostic accuracy of first responders in patients with and without a pulse," Resuscitation, vol. 33, No. 2, pp. 107-116, Dec. 1996.

J. Tibballs and P. Russell, "Reliability of pulse palpation by healthcare personnel to diagnose paediatric cardiac arrest," Resuscitation, vol. 80, No. 1, pp. 61-64, Jan. 2009.

J. Osorio, D. J. Dosdall, R. P. Robichaux, P. B. Tabereaux, and R. E. Ideker, "In a swine model, chest compressions cause ventricular capture and, by means of a long-short sequence, ventricular fibrillation.," Circ. Arrhythm. Electrophysiol., vol. 1, No. 4, pp. 282-289, Oct. 2008.

J. Berdowski, J. G. P. Tijssen, and R. W. Koster, "Chest compressions cause recurrence of ventricular fibrillation after the first successful conversion by defibrillation in out-of-hospital cardiac arrest.," Circ. Arrhythm. Electrophysiol., vol. 3, No. 1, pp. 72-78, Feb. 2010.

R. W. Koster, "Refibrillation during out-of-hospital arrest☐: A frequent event with clinical consequences," Signa Vitae, vol. 5, No. Suppl 1, pp. 66-68, 2010.

J. Osorio, D. J. Dosdall, P. B. Tabereaux, R. P. Robichaux, S. Stephens, J. D. Kerby, R. E. Stickney, S. Pogwizd, and R. E. Ideker, "Effect of chest compressions on ventricular activation.," Am. J. Cardiol., vol. 109, No. 5, pp. 670-674, Mar. 2012.

A. Shiyovich, A. Gerovich, and A. Katz, "Recurrence of Ventricular Fibrillation after Successful Conversion , May be Associated with Immediate Post-Shock Chest Compressions☐: A Case Report," vol. 3, No. 3, pp. 722-726, 2013.

R. W. C. G. R. Wijshoff, T. van der Sar, W. H. Peeters, R. Bezemer, P. Aelen, I. W. F. Paulussen, S. C. M. a Ordelman, A. Venema, P. F. J. van Berkom, R. M. Aarts, P. H. Woerlee, G.-J. Scheffer, and G. J. Noordergraaf, "Detection of a spontaneous pulse in photoplethysmograms during automated cardiopulmonary resuscitation in a porcine model.," Resuscitation, vol. 84, No. 11, pp. 1625-1632, Nov. 2013.

R. Wijshoff, T. Van der Sar, R. Aarts, P. Woerlee, and G. Noordergraaf, "Potential of photoplethysmography to guide pulse checks during cardiopulmonary resuscitation: Observations in an animal study," Resuscitation, vol. 84, p. S1, Oct. 2013.

R. Wijshoff, W. Peeters, A. Venema, R. Aarts, and G. J. Noordergraaf, "A photoplethysmography signal can show presence of a spontaneous pulse at sub-life-supporting blood pressure levels during experimental cardiopulmonary resuscitation," Circulation, vol. 130, No. Suppl 2, p. A137, 2014.

R. W. Neumar, C. W. Otto, M. S. Link, S. L. Kronick, M. Shuster, C. W. Callaway, P. J. Kudenchuk, J. P. Ornato, B. McNally, S. M. Silvers, R. S. Passman, R. D. White, E. P. Hess, W. Tang, D. Davis, E. Sinz, and L. J. Morrison, "Part 8: adult advanced cardiovascular life support: 2010 American Heart Association Guidelines for Cardiopulmonary Resuscitation and Emergency Cardiovascular Care.," Circulation, vol. 122, No. 18 Suppl 3, pp. S729-67, Nov. 2010.

L. A. Geddes et al, Characterization of the oscillometric method for measuring indirect blood pressure, Annals of Biomedical Engineering, vol. 10, pp. 271-280, 1982.

APPARATUS FOR USE IN MEASURING BLOOD PRESSURE

This application is the U.S. National Phase application under 35 U.S.C. § 371 of International Application No. PCT/EP2020/052806, filed on 2 May 2020, which claims the benefit of European Application Serial No. 19156730.4, filed 12 Feb. 2019. These applications are hereby incorporated by reference herein.

FIELD OF THE INVENTION

The disclosure relates to an apparatus, a system and a method for use in measuring blood pressure.

BACKGROUND OF THE INVENTION

High quality cardiopulmonary resuscitation (CPR) requires minimum interruptions to chest compressions. During CPR, chest compressions are interrupted to perform pulse checks, typically by manual palpation for arterial pulsations. Futile pulse checks lead to unnecessary interruptions in chest compressions. Moreover, pulse checks by manual palpation are known to be time-consuming, especially when a spontaneous pulse is absent. This can lead to long interruptions in compressions, which negatively impacts the CPR outcome. An objective method to detect the presence or absence of a spontaneous pulse, especially during ongoing chest compressions, can prevent unnecessary interruptions in chest compressions for futile pulse checks and thereby improve CPR outcome. Furthermore, it is known that delivering compressions on a beating heart may lead to re-arrest. Therefore, it is important to know when in time the heart is sufficiently strong and no longer needs additional support, so that compressions can be stopped.

In automated CPR studies, it has been shown that a photoplethysmography (PPG) signal can indicate the presence or absence of a spontaneous pulse during ongoing chest compressions. Thus, PPG can support detection of return of spontaneous circulation (ROSC). In particular, PPG can indicate whether or not the heart has resumed beating through detection of a self-contained contraction of the heart after arrest and, where the heart has resumed beating, PPG also allows measurement of the pulse rate. Furthermore, PPG can detect presence of spontaneous pulses at sub-life-supporting blood pressures. The PPG-based approach is advantageous as it is unobtrusive and easy to integrate within the CPR procedure. However, a downside of the PPG-based approach is that it does not inherently provide information about the achieved and quantified blood pressure levels. Moreover, an additional or alternative means is required to assess the adequacy of the spontaneous pulse in the PPG signal, which can support the clinician in determining when to continue or stop CPR.

Alternatively, a reliable and objective measurement to ROSC detection is a continuous arterial blood pressure measurement, which can be interpreted to indicate ROSC when the systolic blood pressure is higher than, e.g. 60 mmHg. However, this is an invasive measurement which requires arterial access and placement of catheters and is consequently not always available. Therefore, an improved non-invasive method that can quantitatively support ROSC detection during ongoing chest compressions would be valuable.

U.S. Pat. No. 5,606,977A An automated sphygmomanometer which automatically determines when a blood pressure determination needs to be made. During a "guard mode" determination, a cuff on an appendage of the patient is frequently inflated to a check pressure, which is preferably below the patient's mean arterial pressure ("MAP"), and the signature (shape, amplitude, pulse period, etc.) of the measured oscillometric signal is compared to a stored signature of a portion of an oscillometric signal at a corresponding portion of the oscillometric envelope determined during a previous blood pressure determination. If these signals differ by some predetermined amount, it is determined that the patient's blood pressure has changed significantly and that a new blood pressure determination needs to be conducted immediately. These guard mode determinations are made in addition to the normal blood pressure determinations made at predetermined intervals typically selected by the user. In addition, the shape of the oscillometric signal is quantified during guard mode so that it is possible to discriminate oscillations on the diastolic side of a patient's oscillometric envelope from oscillations on the systolic side of the patient's oscillometric envelope, thereby preventing a large shift in the oscillometric envelope from going undetected.

US 2016/0270673 discloses a CPR device comprising a device configured for tracking the diastolic blood pressure in a patient, where the device applies a pressure to a body part by use of an inflatable cuff. The device is configured to detect ROSC based on the measured blood pressure level. However, although the use of such a device is non-invasive, the device is intended for continuous tracking of the diastolic blood pressure and can thus interfere with CPR. Furthermore, in this approach, prolonged inflation of the cuff can hamper blood flow through the limb, which can be undesirable.

SUMMARY OF THE INVENTION

As noted above, a limitation with existing techniques that enable non-invasive blood pressure measurement for a subject undergoing CPR is that the techniques tend to interfere with the CPR. It would thus be valuable to have an improvement aimed at addressing this limitation.

Therefore, according to a first aspect, there is provided an apparatus for use in measuring blood pressure. The apparatus comprises a processor configured to acquire a signal indicative of pressure oscillations detected inside a cuff inflated to pressurize a measurement site of a subject undergoing cardiopulmonary resuscitation. The pressure oscillations detected inside the cuff are indicative of a pulse of the subject. The processor is also configured to trigger a blood pressure measurement for the subject based on the pressure oscillations detected inside the cuff In some embodiments, the processor may be configured to trigger the blood pressure measurement for the subject when an amplitude of the pressure oscillations detected inside the cuff decreases subsequent to reaching a maximum amplitude. In some embodiments, the processor may be configured to trigger the blood pressure measurement for the subject when the amplitude of the pressure oscillations detected inside the cuff decreases to a predefined fraction of the maximum amplitude. In some embodiments, the predefined fraction of the maximum amplitude may be a fraction that is less than or equal to three quarters of the maximum amplitude.

In some embodiments, the cuff may be inflated up to a predefined pressure. In some embodiments, the predefined pressure may be a pressure in a range from 30 to 70 mmHg.

In some embodiments, a speed with which the cuff is inflated may be adjusted based on a pulse rate of the subject.

In some embodiments, the processor may be configured to, if an amplitude of the pressure oscillations decreases as a pressure in the cuff is increased, stop the blood pressure measurement and/or output an instruction to restart cardiopulmonary resuscitation.

In some embodiments, the processor may be configured to suppress at least one harmonic in the signal indicative of pressure oscillations detected inside the cuff. In some of these embodiments, the at least one harmonic corresponds to a frequency of a compression used in the cardiopulmonary resuscitation.

In some embodiments, the processor may be configured to trigger the blood pressure measurement for the subject while the cuff is maintained at a constant pressure. In some embodiments, the processor may be configured to detect when compressions applied to the subject during the cardiopulmonary resuscitation cease and trigger the blood pressure measurement for the subject when the compressions are detected to cease.

In some embodiments, the processor may be configured to trigger the blood pressure measurement for the subject provided that a blood pressure of the subject is greater than a pressure detected inside the cuff. In some embodiments, the processor may be configured to determine whether the blood pressure of the subject is greater than the pressure inside the cuff based on a morphology of the signal indicative of the pressure oscillations detected inside the cuff and/or data acquired from at least one sensor configured to detect a pulse of the subject.

In some embodiments, the processor may be configured to acquire a plurality of signals indicative of pressure oscillations detected inside a respective plurality of cuffs inflated to pressurize different measurement sites of the subject and trigger the blood pressure measurement for the subject based on the pressure oscillations detected inside the plurality of cuffs.

According to a second aspect, there is provided a system for use in measuring blood pressure. The system comprises the apparatus as described earlier. In some embodiments, the system may also comprise one or more wearable cuffs.

According to a third aspect, there is provided a method for use in measuring blood pressure. The method comprises acquiring a signal indicative of pressure oscillations detected inside a cuff inflated to pressurize a measurement site of a subject undergoing cardiopulmonary resuscitation. The pressure oscillations detected inside the cuff are indicative of a pulse of the subject. The method also comprises triggering a blood pressure measurement for the subject based on the pressure oscillations detected inside the cuff.

According to a fourth aspect, there is provided a computer program product comprising a computer readable medium. The computer readable medium has a computer readable code embodied therein. The computer readable code is configured such that, on execution by a suitable computer or processor, the computer or processor is caused to perform the method described earlier.

According to the aspects and embodiments described above, the limitations of existing techniques are addressed. In particular, according to the above-described aspects and embodiments, information related to blood pressure can be inferred by performing pulse detection using a pressurized cuff and this information can be used to trigger a blood pressure measurement. This allows a fast and non-invasive assessment of blood pressure in a subject undergoing CPR. As the blood pressure of the subject can be measured quickly in this way, the measurement of blood pressure does not interfere with the CPR. There is thus provided an improved apparatus, system and method for use in measuring blood pressure.

These and other aspects will be apparent from and elucidated with reference to the embodiment(s) described hereinafter.

BRIEF DESCRIPTION OF THE DRAWINGS

Exemplary embodiments will now be described, by way of example only, with reference to the following drawings, in which.

DETAILED DESCRIPTION OF EMBODIMENTS

As noted above, there is provided herein an improved apparatus, system and method for use in measuring blood pressure (e.g. arterial blood pressure).

Figure 1:
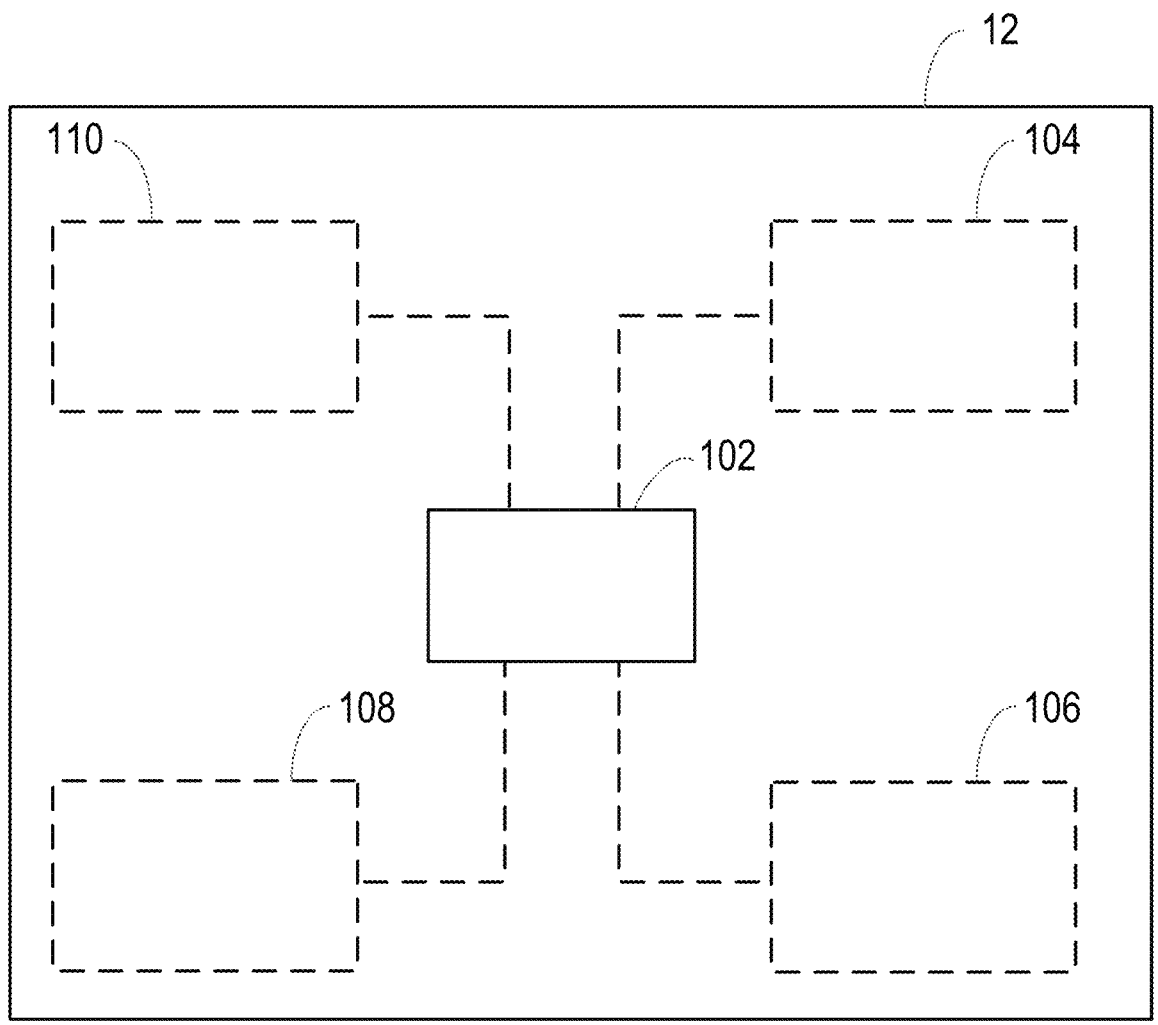
FIG. 1 is an illustration of an apparatus according to an embodiment.

FIG. 1 illustrates an apparatus 12 for use in measuring blood pressure according to an embodiment. As illustrated in FIG. 1, the apparatus 12 described herein comprises a processor 102. Briefly, the processor 102 is configured to acquire a signal indicative of pressure oscillations detected inside a cuff inflated to pressurize a measurement site of a subject undergoing cardiopulmonary resuscitation (CPR). The pressure oscillations detected inside the cuff are indicative of a pulse of the subject. The processor 102 is also configured to trigger a blood pressure measurement for the subject based on the pressure oscillations detected inside the cuff.

The processor 102 can be implemented in numerous ways, with software and/or hardware, to perform the various functions described herein. In particular implementations, the processor 102 can comprise a plurality of software and/or hardware modules, each configured to perform, or that are for performing, individual or multiple steps of the method described herein. The processor 102 may comprise one or more processors (such as one or more microprocessors, one or more multi-core processors and/or one or more digital signal processors (DSPs)), one or more processing units, and/or one or more controllers (such as one or more microcontrollers) that may be configured or programmed (e.g. using software or computer program code) to perform the various functions described herein. The processor 102 may be implemented as a combination of dedicated hardware (e.g. amplifiers, pre-amplifiers, analog-to-digital convertors (ADCs) and/or digital-to-analog convertors (DACs)) to perform some functions and a processor (e.g. one or more programmed microprocessors, DSPs and associated circuitry) to perform other functions.

As illustrated in FIG. 1, in some embodiments, the apparatus 12 can comprise at least one sensor 104 from which the processor 102 can be configured to acquire the signal indicative of pressure oscillations. Alternatively or in addition, at least one sensor 104 from which the processor 102 can be configured to acquire the signal indicative of pressure oscillations may be external to (e.g. separate to or remote from) the apparatus 12. For example, in some embodiments, the at least one sensor 104 may be located inside the cuff. The at least one sensor 104 referred to herein is configured to obtain the signal indicative of pressure oscillations. Thus, the at least one sensor 104 may also be referred to as at least one pressure sensor. The at least one sensor 104 may be a single sensor or a plurality (e.g. a series or array) of sensors.

Examples of the at least one sensor 104 include, but are not limited to, at least one pressure sensor (such as any one or more of a piezoresistive transducer, a piezoelectric transducer, and a capacitive transducer), or any other sensor or combination of sensors suitable for obtaining a signal indicative of pressure oscillations. A person skilled in the art will be aware of a variety of sensors suitable for obtaining a signal indicative of pressure oscillations and the manner in which those sensors may be configured to operate to obtain the signal indicative of pressure oscillations.

As illustrated in FIG. 1, in some embodiments, the apparatus 12 may comprise at least one memory 106. Alternatively or in addition, at least one memory 106 may be external to (e.g. separate to or remote from) the apparatus 12. For example, a hospital database may comprise at least one memory 106, at least one memory 106 may be a cloud computing resource, or similar. The processor 102 of the apparatus 12 may be configured to communicate with and/or connect to at least one memory 106. A memory 106 may comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM), and electrically erasable PROM (EEPROM). In some embodiments, at least one memory 106 can be configured to store program code that can be executed by the processor 102 of the apparatus 12 to cause the apparatus 12 to operate in the manner described herein.

Alternatively or in addition, in some embodiments, at least one memory 106 can be configured to store information required by or resulting from the method described herein. For example, in some embodiments, at least one memory 106 may be configured to store any one or more of the acquired signal indicative of pressure oscillations, one or more blood pressure measurements for the subject, a pulse rate measurement, or any other information, or any combination of information, required by or resulting from the method described herein. In some embodiments, the processor 102 of the apparatus 12 can be configured to control at least one memory 106 to store information required by or resulting from the method described herein.

As illustrated in FIG. 1, in some embodiments, the apparatus 12 may comprise a user interface 108. Alternatively or in addition, the user interface 108 may be external to (e.g. separate to or remote from) the apparatus 12. The processor 102 of the apparatus 12 may be configured to communicate with and/or connect to a user interface 108. In some embodiments, the processor 102 of the apparatus 12 can be configured to control the user interface 108 to operate in the manner described herein.

The user interface 108 can be configured to render (or output, display, or provide) information required by or resulting from the method described herein. For example, in some embodiments, the user interface 108 may be configured to render (or output, display, or provide) the acquired signal indicative of pressure oscillations, one or more blood pressure measurements for the subject, a pulse rate measurement, and/or any other information, or any combination of information, required by or resulting from the method described herein. Alternatively or in addition, the user interface 108 can be configured to receive a user input. For example, the user interface 108 may allow a user to manually enter information or instructions, interact with and/or control the apparatus 12. Thus, the user interface 108 may be any user interface that enables the rendering (or outputting, displaying, or providing) of information and, alternatively or in addition, enables a user to provide a user input.

For example, the user interface 108 may comprise one or more switches, one or more buttons, a keypad, a keyboard, a mouse, a touch screen or an application (for example, on a smart device such as a tablet, a smartphone, or any other smart device), a display or display screen, a graphical user interface (GUI) such as a touch screen, or any other visual component, one or more speakers, one or more microphones or any other audio component, one or more lights (such as light emitting diode LED lights), a component for providing tactile or haptic feedback (such as a vibration function, or any other tactile feedback component), an augmented reality device (such as augmented reality glasses, or any other augmented reality device), a smart device (such as a smart mirror, a tablet, a smart phone, a smart watch, or any other smart device), or any other user interface, or combination of user interfaces. In some embodiments, the user interface that is controlled to render information may be the same user interface as that which enables the user to provide a user input.

As illustrated in FIG. 1, in some embodiments, the apparatus 12 may comprise a communications interface (or communications circuitry) 110. Alternatively or in addition, the communications interface 110 may be external to (e.g. separate to or remote from) the apparatus 12. The communications interface 110 can be for enabling the apparatus 12, or components of the apparatus 12, to communicate with and/or connect to one or more other components (e.g. one or more sensors, interfaces, devices, processors, or memories), such as any of those described herein. For example, the communications interface 110 can be for enabling the processor 102 of the apparatus 12 to communicate with and/or connect to any one or more of the at least one sensor 104 mentioned earlier, the at least one memory 106 mentioned earlier, and the user interface 108 mentioned earlier.

The communications interface 110 may enable the apparatus 12, or components of the apparatus 12, to communicate and/or connect in any suitable way. For example, the communications interface 110 may enable the apparatus 12, or components of the apparatus 12, to communicate and/or connect wirelessly, via a wired connection, or via any other communication (or data transfer) mechanism. In some wireless embodiments, for example, the communications interface 110 may enable the apparatus 12, or components of the apparatus 12, to use radio frequency (RF), Bluetooth, or any other wireless communication technology to communicate and/or connect.

Figure 2:
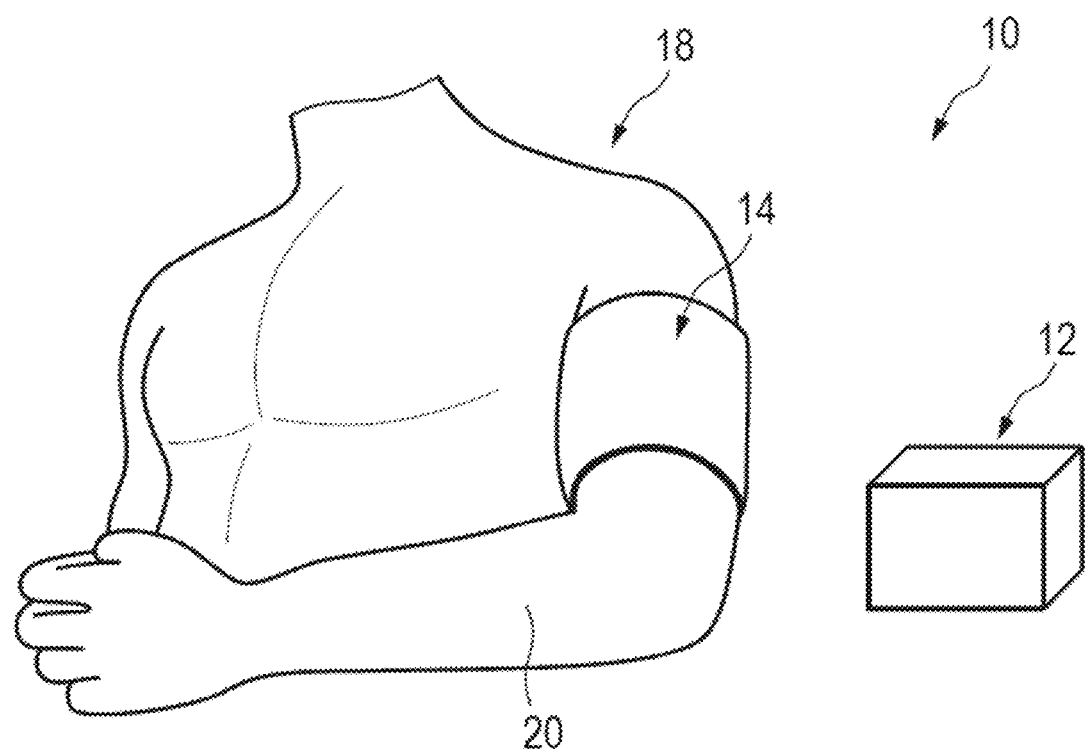
FIG. 2 is an illustration of a system according to an embodiment.

FIG. 2 illustrates a system 10 for use in measuring blood pressure according to an embodiment. As illustrated in FIG. 2, the system 10 comprises the apparatus 12 described herein. As also illustrated in FIG. 2, the system 10 can further comprise a wearable cuff 14 (or clamp unit). The wearable cuff 14 referred to herein is for use in measuring blood pressure. The wearable cuff 14 can be for use in non-invasive blood pressure (NIBP) measurements, such as inflation-based NIBP (iNIBP) measurements.

The wearable cuff 14 is configured to be worn on or around (e.g. wrapped around, attached to, or fastened to) a measurement site 20 of a subject (e.g. a patient) 18. The subject 18 referred to herein is a subject that is undergoing CPR. The subject 18 can be, for example, an adult or a pediatric subject, e.g. an infant, a child or an adolescent. An infant can, for example, be a neonate, such as a pre-term or premature infant, a full-term infant or a post-term infant.

The measurement site 20 of the subject 18 can be any site on the body of the subject 18 that is suitable for use in measuring a blood pressure of the subject 18, such as any site on the body of the subject 18 that comprises an artery. For example, the measurement site 20 of the subject 18 may be located on a limb of the subject 18, such as an arm (e.g. an upper arm or a forearm) of the subject 18, a leg of the subject 18, a finger of the subject 18, or any other limb of the subject 18 that is suitable for use in measuring a blood pressure of the subject 18. Thus, the wearable cuff 14 can be configured to be worn on or around (e.g. wrapped around, attached to, or fastened to) a limb of the subject 18. In the embodiment illustrated in FIG. 2, the measurement site 20 of the subject 18 is located on the arm (or, more specifically, the upper arm) of the subject 18. Thus, the cuff 14 is worn on or around (e.g. wrapped around, attached to, or fastened to) the arm of the subject 18 in the illustrated embodiment of FIG. 2.

The wearable cuff 14 is inflatable to pressurize the measurement site 20 of the subject 18. In this way, the wearable cuff 14 can pressurize an artery in the measurement site 20 of the subject 18. Typically, the wearable cuff 14 can be supplied with a fluid (e.g. a gas, such as air, or any other fluid) suitable for inflating the wearable cuff 14. The wearable cuff 14 can be inflatable to pressurize the measurement site 20 of a subject 18 (and thus an artery in the measurement site 20 of the subject 18) at the pressure of the fluid in the wearable cuff 14. Although the system 10 of FIG. 2 is illustrated as comprising a single wearable cuff 14, it will be appreciated that the system 10 may comprise one or more wearable cuffs 14. Thus, the apparatus 12 described herein can be for use with one or more wearable cuffs 14.

Figure 3:
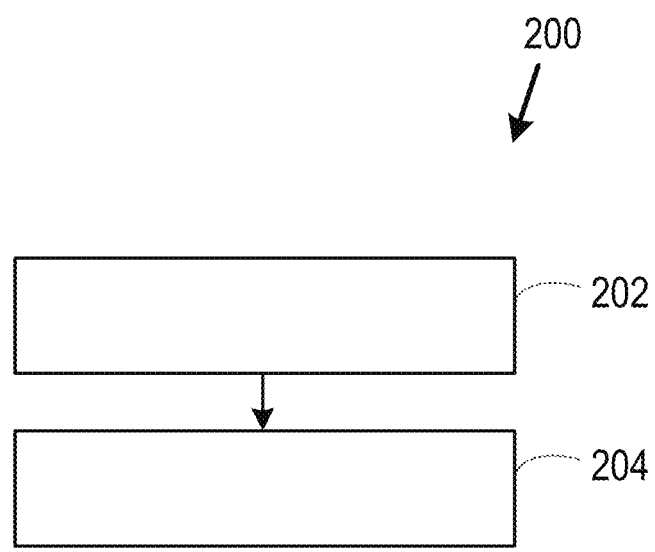
FIG. 3 is a flow chart illustrating a method according to an embodiment.

FIG. 3 illustrates a method 200 for use in measuring blood pressure according to an embodiment. More specifically, FIG. 3 illustrates a method 200 of operating the apparatus 12 described herein for use in measuring blood pressure. The method 200 is a computer-implemented method. As described earlier, the apparatus 12 comprises a processor 102. The method 200 illustrated in FIG. 3 can generally be performed by or under the control of the processor 102 of the apparatus 12.

With reference to FIG. 3, at block 202 of FIG. 3, a signal indicative of pressure oscillations detected inside a cuff 14 inflated to pressurize a measurement site 20 of a subject 18 is (e.g. automatically) acquired. More specifically, the processor 102 of the apparatus 12 acquires the signal indicative of pressure oscillations detected inside the cuff 14.

In some embodiments, the signal indicative of pressure oscillations detected inside the cuff 14 may be acquired by filtering (e.g. band-pass filtering) a signal indicative of a pressure detected inside the cuff 14. Thus, in some embodiments, a filter (e.g. a band-pass filter) may be used to filter the signal indicative of the pressure detected inside the cuff 14 to acquire the signal indicative of pressure oscillations detected inside a cuff 14. The filter may be a filter that is designed based on one or more requirements related to blood pressure measurement, e.g. NIBP measurement or iNIBP measurement. The signal indicative of the pressure detected inside the cuff 14 may be referred to as the "pressure signal", whereas the signal indicative of pressure oscillations detected inside the cuff 14 may be referred to as the "oscillation signal" or "pressure oscillation signal".

As mentioned earlier, the pressure oscillations detected inside the cuff 14 are indicative of a pulse of the subject 18. If the heart of the subject 18 is beating, the subject 18 has a pulse and thus pressure oscillations are detected inside the cuff 14. Thus, the cuff 14 can be used for pulse detection. The pressure oscillations detected inside the cuff 14 may result from larger arteries (e.g. the brachial artery) and thus the signal indicative of pressure oscillations detected inside the cuff 14 may reflect the beating heart of the subject 18 in case of centralization. As mentioned earlier, the subject 18 referred to herein is a subject that is undergoing cardiopulmonary resuscitation (CPR). Thus, the cuff 14 can be inflated to pressurize the measurement site 20 of the subject 18 during CPR. In some embodiments, the signal indicative of pressure oscillations detected inside the cuff 14 may be acquired during CPR.

Although not illustrated in FIG. 3, in some embodiments, the processor 102 may be configured to suppress at least one harmonic in the signal indicative of pressure oscillations detected inside the cuff 14. The at least one harmonic may correspond to a frequency of a compression used in the CPR. The frequency of compression may be obtained (e.g. directly) from a device used to perform the CPR or determined from a transthoracic impedance signal, a chest compression acceleration, a velocity or depth, a chest compression force, an alternative acceleration signal indicative of chest compressions, or a radar signal indicative of chest compressions. By suppressing at least one harmonic that corresponds to a frequency of a compression used in the CPR, the signal indicative of pressure oscillations detected inside the cuff 14 provides a more accurate representation of the pulse of the subject 18. Thus, it is possible to facilitate pulse detection with a cuff 14 even during CPR.

Alternatively, in some embodiments, the signal indicative of pressure oscillations detected inside the cuff 14 may be acquired while CPR is paused (e.g. during a ventilation pause, which may be a few seconds) or only the signal indicative of pressure oscillations detected inside the cuff 14 acquired while CPR is paused may be used (e.g. the signal may be gated). In these embodiments, the processor 102 may be configured to detect when compressions applied to the subject during the CPR cease. That is, the processor 102 may be configured to detect cessation of compressions applied to the subject 18 during the CPR. The processor 102 may, for example, acquire one or more additional signals (e.g. accelerometer, force, radar and/or impedance signals) indicative of the compressions. In this way, pulse detection and subsequent analysis can be enhanced.

In some embodiments, the cuff 14 may be inflated up to a predefined (or known) pressure. The predefined pressure may also be referred to as a baseline pressure. The predefined pressure may be set (e.g. programmed) in the apparatus 10. The predefined pressure may be a pressure that is sufficiently high to ensure the cuff 14 has an acceptable sensitivity to artery pulsations. At the same time, the predefined pressure may not exceed a maximum pressure above which blood flow is blocked in order to prevent the blockage of blood flow after successful CPR therapy. For example, in some embodiments, the predefined pressure may, for example, be a pressure in a range from 30 to 70 mmHg, for example a pressure in a range from 35 to 65 mmHg, for example a pressure in a range from 40 to 60 mmHg, for example a pressure in a range from 45 to 55 mmHg.

Returning to FIG. 3, at block 204, a blood pressure measurement for the subject 18 is (e.g. automatically) triggered based on the pressure oscillations detected inside the cuff 14. More specifically, the processor 102 of the apparatus 12 triggers the blood pressure measurement for the subject 18 based on the pressure oscillations detected inside the cuff 14. In this way, information related to blood pressure can be inferred by performing pulse detection using a pressurized cuff and this information can be used to trigger a blood pressure measurement. This allows a fast assessment of blood pressure in a subject 18 undergoing CPR. Through the use of the cuff 14, the blood pressure measurement is a non-invasive blood pressure (NIBP) measurement.

In some embodiments, the processor 102 can be configured to trigger the blood pressure measurement for the subject 18 when an amplitude of the pressure oscillations detected inside the cuff 14 (e.g. substantially) decreases subsequent to reaching a maximum amplitude. For example, it can be assumed that a diastolic blood pressure of the subject 18 has risen above the pressure inside the cuff 14 when the amplitude of the pressure oscillations detected inside the cuff 14 (e.g. substantially) decreases subsequent to reaching the maximum amplitude. This decrease in amplitude of the pressure oscillations may be detected in the acquired signal indicative of the pressure oscillations or in an envelope of the pressure oscillations. The envelope of the pressure oscillations is a curve or line outlining the amplitude of the pressure oscillations over time, e.g. calculated based on the extremes (i.e.

maxima and/or minima) of the signal indicative of pressure oscillations. The envelope of the pressure oscillations can, for example, be obtained by applying maxima (e.g. peak) and minima (e.g. valley) detection on the signal indicative of pressure oscillations.

In some of these embodiments, the processor 102 may be configured to trigger the blood pressure measurement for the subject 18 when the amplitude of the pressure oscillations detected inside the cuff 14 decreases to a predefined fraction of the maximum amplitude. In some embodiments, the predefined fraction of the maximum amplitude may be a fraction that is less than or equal to three quarters (¾) of the maximum amplitude. For example, in some embodiments, the predefined fraction of the maximum amplitude may be a fraction that is less than or equal to seven tenths (⁷⁄₁₀) of the maximum amplitude, for example a fraction that is less than or equal to two thirds (⅔) of the maximum amplitude, for example a fraction that is less than or equal to three fifths (⅗) of the maximum amplitude, for example a fraction that is less than or equal to five ninths (⁵⁄₉) of the maximum amplitude, for example a fraction that is less than or equal to half (½) of the maximum amplitude.

Alternatively, in other embodiments, the processor 102 may be configured to trigger the blood pressure measurement for the subject 18 when the amplitude of the pressure oscillations detected inside the cuff 14 decreases to a predefined percentage of the maximum amplitude. In some embodiments, the predefined percentage of the maximum amplitude may be a percentage that is less than or equal to 75% of the maximum amplitude. For example, in some embodiments, the predefined fraction of the maximum amplitude may be a percentage that is less than or equal to 70% of the maximum amplitude, for example a percentage that is less than or equal to 65% of the maximum amplitude, for example a percentage that is less than or equal to 60% of the maximum amplitude, for example a percentage that is less than or equal to 55% of the maximum amplitude, for example a percentage that is less than or equal to 50% of the maximum amplitude.

In some embodiments, the processor 102 can be configured to trigger the blood pressure measurement for the subject 18 while the cuff 14 is maintained at a constant (positive) pressure. The constant pressure can be the predefined pressure mentioned earlier up to which the cuff 14 is inflated. Thus, the constant pressure may be a pressure that is sufficiently high to ensure the cuff 14 has an acceptable sensitivity to artery pulsations. At the same time, the constant pressure may not exceed a maximum pressure above which blood flow is blocked in order to prevent the blockage of blood flow after successful CPR therapy. For example, in some embodiments, the constant pressure may, for example, be a pressure in a range from 30 to 70 mmHg, for example a pressure in a range from 35 to 65 mmHg, for example a pressure in a range from 40 to 60 mmHg, for example a pressure in a range from 45 to 55 mmHg. In some embodiments, the cuff 14 may be further inflated upon or (e.g. immediately) after triggering of the blood pressure measurement for the subject 18. In this way, the blood pressure of the subject 18 can be measured during inflation of the cuff 14. That is, the blood pressure measurement can be an iNIBP measurement.

The blood pressure of the subject 18 may be measured in any suitable way and a person skilled in the art will be aware of various ways in which to measure blood pressure. For example, the amplitude of the pressure oscillations detected inside the cuff 14 contains information about the blood pressure, e.g. the amplitude of the pressure oscillations detected inside the cuff 14 is highest when the cuff pressure is approximately equal to the mean arterial blood pressure (MAP).

Although not illustrated in FIG. 3, in some embodiments, a speed with which the cuff 14 is inflated (or the inflation rate of the cuff 14) may be adjusted based on a pulse rate of the subject 18. Herein, the speed with which the cuff 14 is inflated (or the inflation rate of the cuff 14) can be defined as the amount of pressure increase in the cuff 14 per unit of time, e.g. mmHg per second. Thus, according to some embodiments, the speed with which the cuff 14 is inflated can be related to the pulse rate of the subject 18. For example, in some embodiments, the speed with which the cuff 14 is inflated may be adjusted linearly with the pulse rate of the subject 18. Thus, according to these embodiments, the speed with which the cuff 14 is inflated is linearly related to the pulse rate of the subject 18. That is, for example, the speed with which the cuff 14 is inflated may be X mmHg per heartbeat. The value of X (and thus the speed with which the cuff 14 is inflated) may, for example, be a value in a range from 5 to 20 mmHg per heartbeat, for example a value in a range from 7 to 18 mmHg per heartbeat, for example a value in a range from 9 to 16 mmHg per heartbeat, for example a value in a range from 11 to 14 mmHg per heartbeat. The speed with which the cuff 14 is inflated (e.g. the value of X) may be selected depending on the desired accuracy for the blood pressure measurement. By adjusting the speed with which the cuff 14 is inflated based on the pulse rate of the subject 18, the time needed to obtain the blood pressure measurement is minimized.

A reduction in the blood pressure measurement time may be achieved in several other ways, any of which may be combined. For example, the speed of the blood pressure measurement may be increased to reduce the blood pressure measurement time. This may provide a blood pressure measurement with lower accuracy and robustness. However, in some situations, a fast (yet crude) estimate of blood pressure may be beneficial compared to a longer blood pressure measurement. Alternatively or in addition, the blood pressure measurement may be stopped prior to systolic blood pressure detection. For example, it may be sufficient to only detect MAP, which only requires the detection of the maximum amplitude of the pressure oscillations detected inside the cuff 14. Thus, once the pressure oscillations detected inside the cuff 14 begin to decrease, the blood pressure measurement may be stopped. Alternatively or in addition, the predefined fraction (or percentage) described earlier that can be used in triggering the pressure measurement according to some embodiments may be adjusted to a higher level, e.g. a higher level than two thirds (or a higher level than 65%). This means that the blood pressure measurement is triggered earlier, e.g. when the pressure inside the cuff 14 is just below MAP but around (or even slightly above) diastolic blood pressure. Although this may reduce the accuracy of a diastolic blood pressure measurement, the accuracy of the systolic blood pressure measurement is unaffected.

If the diastolic blood pressure of the subject 18 is above the predefined pressure up to which the cuff 14 is inflated, the amplitude of the pressure oscillations detected inside the cuff 14 will increase as the pressure in the cuff 14 is increased over the course of the blood pressure measurement, as the maximum oscillation will be reached when the pressure in the cuff 14 is approximately equal to the MAP. If the amplitude of the pressure oscillations detected inside the cuff 14 decreases as the pressure inside the cuff 14 is increased, the processor 102 may be configured to (e.g. immediately) stop the blood pressure measurement. It may then be necessary to reapply CPR therapy.

In some embodiments, in the case of manual CPR, this information may be displayed to a user. For example, the processor 102 can be configured to control a user interface 108 (such as a user interface of the apparatus 12 or a user interface external to the apparatus 12) to display this information to the user. In other embodiments, in the case of automated CPR, a feedback loop may cause the chest compressions to restart (e.g. immediately). For example, the processor 102 can be configured to control a CPR device used in the CPR therapy to restart the chest compressions. Alternatively, in the case of automated CPR, an instruction may be provided to a user to instruct the user to restart the compressions with the CPR device. For example, the processor 102 can be configured to control a user interface 108 (such as a user interface of the apparatus 12 or a user interface external to the apparatus 12) to render such an output to the user.

Although not illustrated in FIG. 3, in some embodiments, the processor 102 may be configured to detect when compressions applied to the subject during the CPR cease. That is, the processor 102 may be configured to detect cessation of compressions applied to the subject 18 during the CPR. The processor 102 may, for example, acquire one or more additional signals (e.g. accelerometer, force, radar and/or impedance signals) indicative of the compressions. In this way, pulse detection and subsequent analysis can be enhanced. In some of these embodiments, the processor 102 may be configured to trigger the blood pressure measurement for the subject 18 when the compressions are detected to cease.

Although the processor 102 has been described earlier as being configured to acquire "a" signal indicative of pressure oscillations detected inside "a" cuff 14 inflated to pressurize "a" measurement site 20 of a subject 18, it will be appreciated that the processor 102 can be configured to acquire a plurality of signals indicative of pressure oscillations detected inside a respective plurality of cuffs 14 inflated to pressurize different measurement sites 20 of the subject 18. The different measurement sites 20 of the subject 18 may be on the same limb of the subject 18 and/or on different limbs of the subject. In some of these embodiments, the processor 102 may be configured to trigger the blood pressure measurement for the subject 18 based on the pressure oscillations detected inside the plurality of cuffs 14. In some embodiments, the one or more of the plurality of cuffs 14 may be inflated up to different predefined pressures. In this way, it is possible to better estimate whether the blood pressure of the subject 18 has increased beyond the pressure up to which the cuff 14 is inflated.

Although not illustrated in FIG. 3, in some embodiments, the processor 102 may be configured to, if an amplitude of the pressure oscillations detected inside the cuff 14 decreases as a pressure in the cuff 14 is increased, stop the blood pressure measurement. Alternatively or in addition, in some embodiments, the processor 102 may be configured to, if an amplitude of the pressure oscillations detected inside the cuff 14 decreases as a pressure in the cuff 14 is increased, output an instruction to restart CPR. In some embodiments, the processor 102 may be configured to control a user interface 108 (such as a user interface of the apparatus 12 or a user interface external to the apparatus 12) to output the instruction to restart CPR. For example, the instruction to restart CPR may be output on a display.

Figure 4:
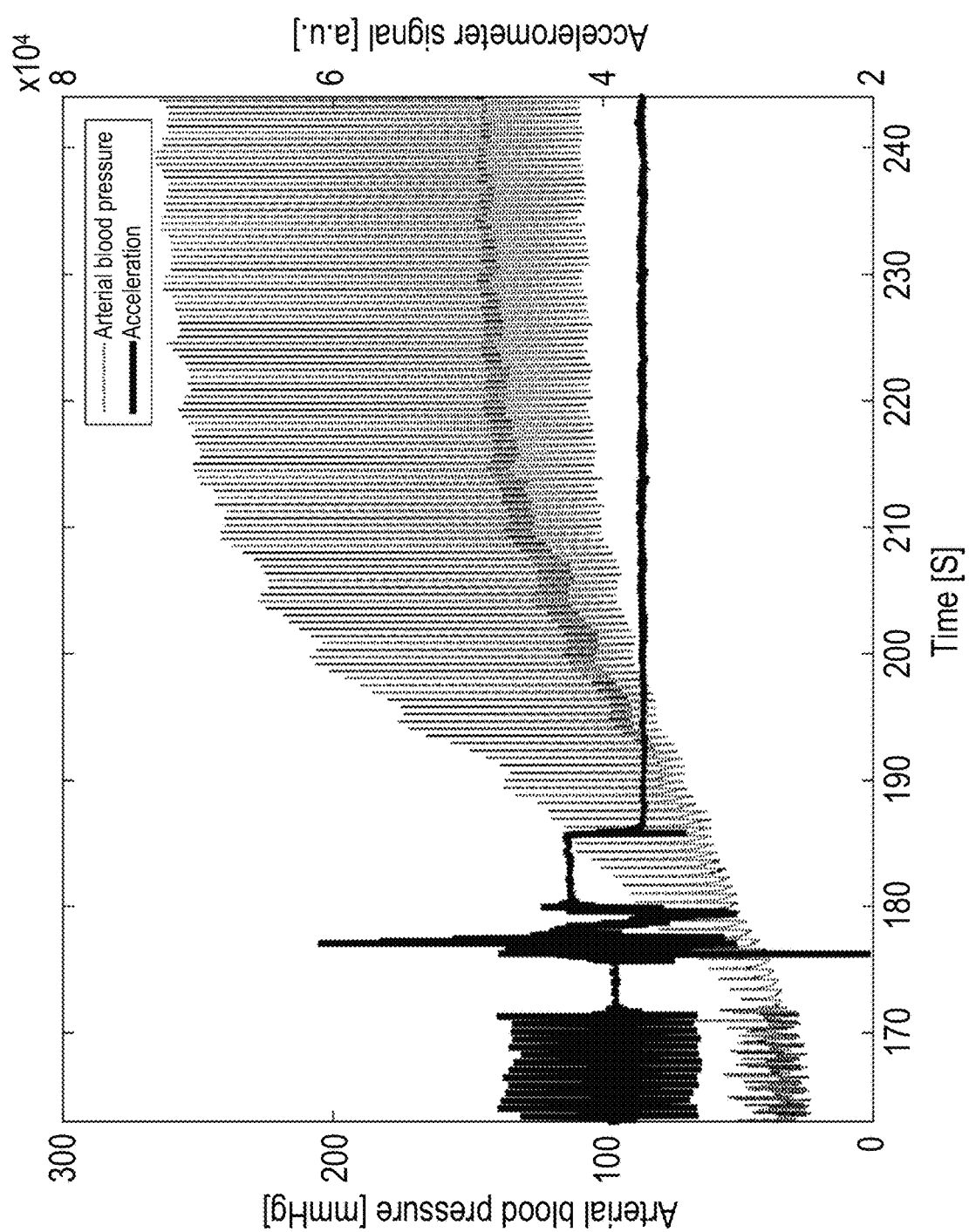
FIG. 4 is an illustration of a blood pressure measurement and an accelerometer signal as a function of time.

FIG. 4 illustrates an invasively obtained raw arterial blood pressure measurement for a subject 18 (in mmHg) as a function of time (in seconds) and an accelerometer signal (in an arbitrary unit) as a function of time. The accelerometer signal is indicative of compressions applied to the chest of the subject 18. After the compressions are stopped, the blood pressure rises to acceptable levels as the heart effectively restarts, which indicates that the CPR therapy has been successful. That is, ROSC has been achieved.

Figure 5:
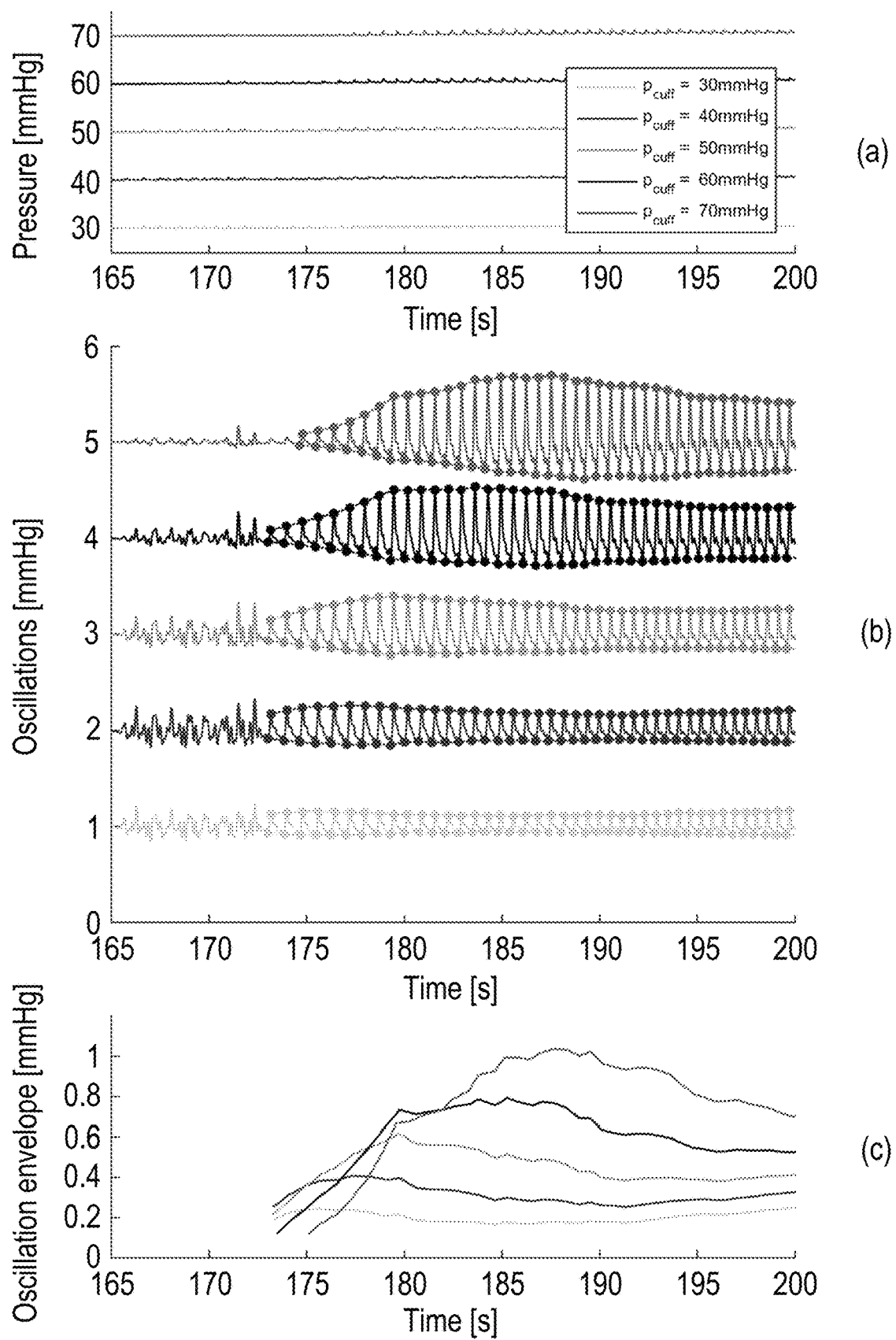
FIG. 5 is an illustration of various signals for a cuff as a function of time.

An example of the resulting pressure signals for the cuff 14 as a function of time are illustrated in FIG. 5. In more detail, FIG. 5(a) illustrates signals indicative of a pressure inside a cuff 14 inflated to pressurize a measurement site of the subject 18 (in mmHg) as a function of time (in seconds), for different predefined pressures $P_{cuff}$ up to which the cuff 14 may be inflated. The signals illustrated in FIG. 5(a) are signals that are simulated based on the raw arterial blood pressure measurement for the subject 18 illustrated in FIG. 4. That is, the "ground truth" blood pressure measurement data of FIG. 4 is used to simulate the dynamic cuff pressure signals of FIG. 5(a) for different predefined cuff pressure values. The pressure inside the cuff 14 equals the predefined pressure plus a (small) pressure oscillation signal. FIG. 5(b) illustrates respective signals indicative of the pressure oscillations inside the cuff 14 inflated to pressurize the measurement site of the subject 18 (in mmHg) as a function of time (in seconds) for the different predefined pressures $P_{cuff}$. For visualization purposes, a 1mmHg offset was added between the different curves. FIG. 5(c) illustrates respective signals showing the envelope of the pressure oscillations inside the cuff 14 inflated to pressurize the measurement site of the subject 18 (in mmHg) as a function of time (in seconds) for the different predefined pressures $P_{cuff}$. The different predefined pressures $P_{cuff}$ are 30 mmHg, 40 mmHg, 50 mmHg, 60 mmHg, and 70 mmHg. The predefined pressures remain constant over time in FIGS. 5(a), (b) and (c).

In this example, a band-pass filter is used to acquire the signals of FIG. 5(b) indicative of the pressure oscillations inside the cuff 14 from the respective signals of FIG. 5(a) indicative of the pressure inside the cuff 14. However, it will be understood that the signals indicative of the pressure oscillations may be acquired from the signals indicative of the pressure inside the cuff 14 in other ways. The envelope of the pressure oscillations is a curve or line outlining the amplitude of the pressure oscillations over time, e.g. calculated based on the extremes (i.e. maxima and/or minima) of the signal indicative of pressure oscillations. The envelope of the pressure oscillations can, for example be obtained by applying maxima (e.g. peak) and minima (e.g. valley) detection on the signal indicative of pressure oscillations.

As illustrated in FIG. 5, immediately after compressions are stopped (at approximately 172 seconds), pressure oscillations can be observed. These pressure oscillations result from arterial blood pressure oscillations observed after CPR therapy and generated by the beating heart. The pressure oscillations have an amplitude that depends on the predefined pressure $P_{cuff}$ up to which the cuff 14 is inflated. It can be seen that pressure oscillations indicative of a pulse of the subject 18 are quickly detected for all of the predefined pressures $P_{cuff}$ in the range from 30 to 70 mmHg. The rapid detection of pressure oscillations indicative of a pulse of the subject 18 is beneficial in order to rapidly determine whether the subject 18 requires additional CPR therapy, since prolonged hypotensive periods can cause lasting damage to the vital functions (e.g. brain) of the subject 18 and eventually death. The simulation confirms that a cuff 14 at a constant pressure can be used to detect the presence of a pulse quickly (e.g. in a few seconds). As such, it is possible for the detection of the pulse to be made in ventilation pauses in CPR (e.g. in 30:2 CPR).

Figure 6:
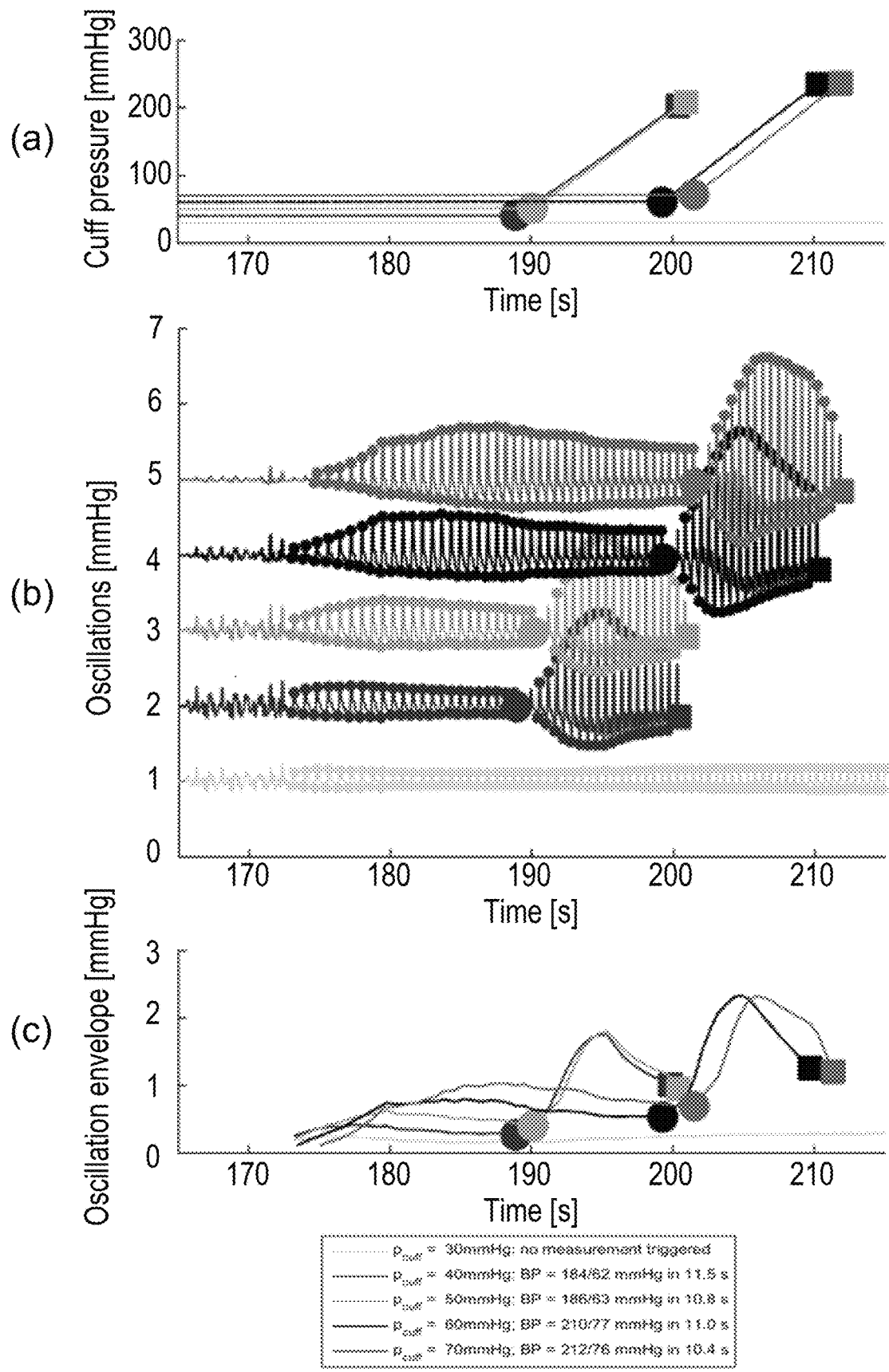
FIG. 6 is an illustration of various signals for a cuff as a function of time.
Figure 6:
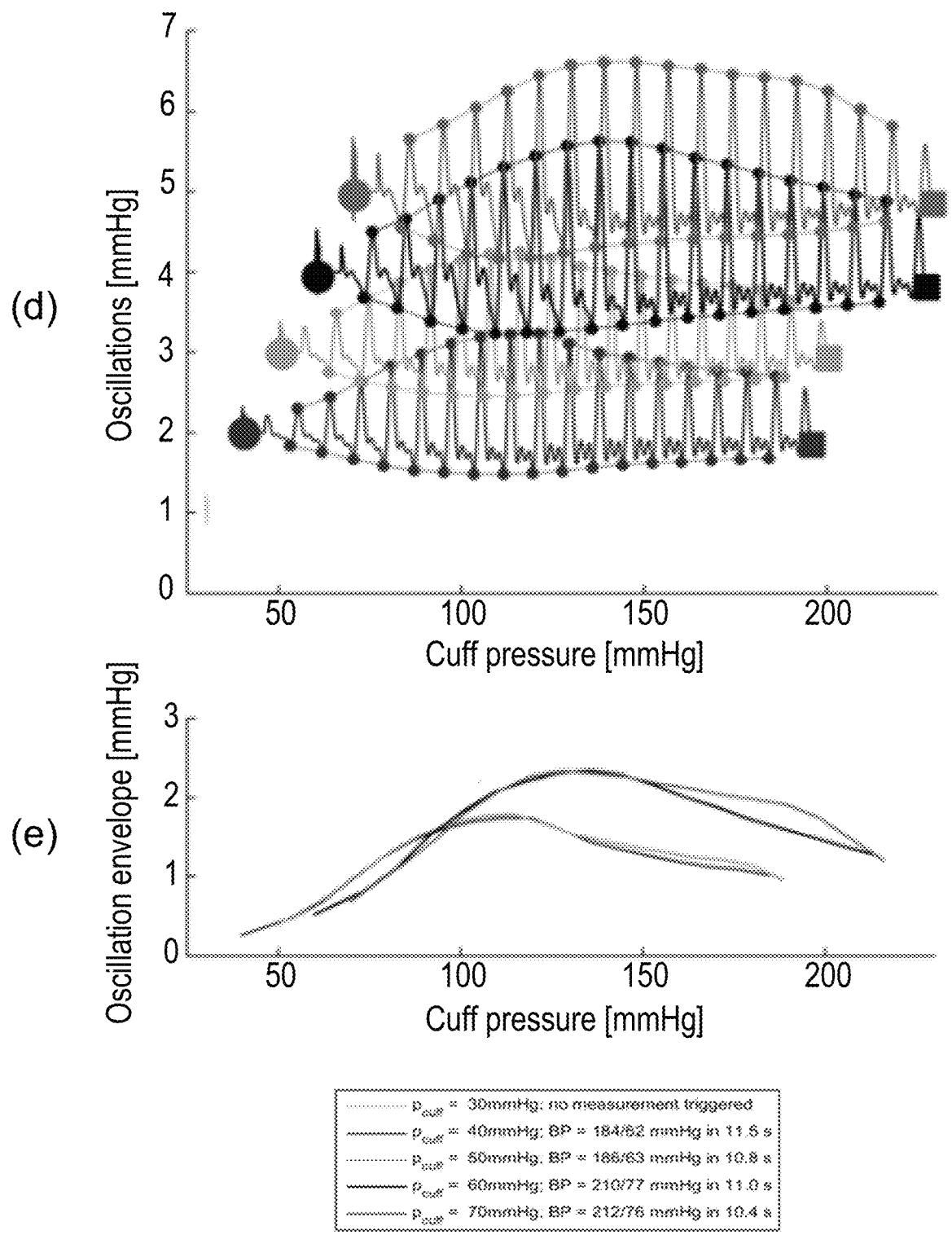

Another example of the resulting pressure signals for the cuff 14 as a function of time are illustrated in FIG. 6. More specifically, FIGS. 6(a), (b) and (c) illustrate the same signals as FIGS. 5(a), (b) and (c) respectively but on an extended time scale. That is, FIG. 6(a) illustrates the signals indicative of the pressure inside the cuff 14 inflated to pressurize a measurement site of the subject 18 (in mmHg) as a function of time (in seconds) for the different predefined pressures $P_{cuff}$ up to which the cuff 14 may be inflated, FIG. 6(b) illustrates the respective signals indicative of the pressure oscillations inside the cuff 14 inflated to pressurize the measurement site of the subject 18 (in mmHg) as a function of time (in seconds) for the different predefined pressures $P_{cuff}$ and FIG. 6(c) illustrates the respective signals showing the envelope of the pressure oscillations inside the cuff 14 inflated to pressurize the measurement site of the subject 18 (in mmHg) as a function of time (in seconds) for the different predefined pressures $P_{cuff}$. The different predefined pressures $P_{cuff}$ are 30 mmHg, 40 mmHg, 50 mmHg, 60 mmHg, and 70 mmHg.

The earlier description of FIGS. 5(a), (b) and (c) thus also applies to FIGS. 6(a), (b) and (c) respectively. However, in the example illustrated in FIG. 6, the method described herein for triggering a blood pressure measurement is applied. That is, in the example illustrated in FIG. 6, the blood pressure measurement is triggered based on the pressure oscillations detected inside the cuff 14 in the manner described herein. FIG. 6(d) illustrates the respective signals indicative of pressure oscillations inside the cuff 14 inflated to pressurize the measurement site of the subject 18 (in mmHg) as a function of the pressure inside the cuff 14 (in mmHg) during the blood pressure measurement. FIG. 6(e) illustrates the respective signals showing the envelope of the pressure oscillations inside the cuff 14 inflated to pressurize the measurement site of the subject 18 (in mmHg) as a function of the pressure inside the cuff 14 (in mmHg) during the blood pressure measurement.

Assuming that the predefined pressure up to which the cuff 14 is inflated is set to a level beyond the initial systolic blood pressure, but below a more healthy blood pressure level, the blood pressure will increase from below the predefined pressure to above the predefined pressure in case of successful CPR therapy. As illustrated in FIG. 6(c), the amplitude of the pressure oscillations detected inside the cuff 14 reaches a maximum and then starts to decrease, as the blood pressure of the subject 18 exceeds the predefined pressure up to which the cuff 14 is inflated. As described earlier, in some embodiments, the processor 102 can be configured to trigger the blood pressure measurement for the subject 18 when the amplitude of the pressure oscillations detected inside the cuff 14 decreases subsequent to reaching a maximum amplitude.

In this example, the processor 102 is configured to trigger the blood pressure measurement for the subject 18 when the amplitude of the pressure oscillations detected inside the cuff 14 decreases to two thirds (⅔) of the maximum amplitude. The point at which the blood pressure measurement is triggered is indicated by the circles in FIG. 6. At this point, it is assumed that the blood pressure (in particular, the diastolic blood pressure) of the subject 18 has increased above the predefined pressure up to which the cuff 14 is inflated.

As mentioned earlier, the cuff 14 may be further inflated upon or (e.g. immediately) after triggering of the blood pressure measurement for the subject 18 and this is the case in the example illustrated in FIG. 6. In particular, as illustrated in FIG. 6(a) the pressure inside the cuff 14 remains constant over time at the respective predefined pressures until the point at which the blood pressure measurement is triggered in the manner described herein (as indicated by the circles in FIG. 6). At this point, the pressure inside the cuff 14 increases (e.g. linearly) beyond the predefined pressure. In this way, the blood pressure of the subject 18 can be measured during inflation of the cuff 14. In the example illustrated in FIG. 6, the pressure inside the cuff 14 increases until the blood pressure measurement is complete.

The point at which the blood pressure measurement is complete is indicated by the squares in FIG. 6.

The blood pressure measurement is faster than normal since it can be started from a baseline pressure, namely the predefined pressure up to which the cuff 14 is inflated.

In particular, the blood pressure (or, more specifically, the diastolic blood pressure) of the subject 18 is assumed to be larger than the predefined pressure up to which the cuff 14 is inflated and thus there is no need to deflate the cuff 14 prior to performing the blood pressure measurement.

As described earlier, the speed with which the cuff 14 is inflated may be adjusted based on a pulse rate of the subject 18. Thus, the speed can be tuned to the pulse rate of the subject 18. This enables an even faster blood pressure measurement. For example, a blood pressure measurement can be acquired in approximately 10-11 seconds in the example shown in FIG. 6 (e.g. compared to approximately 45 seconds in the existing techniques), with a blood pressure measurement speed of 9 mmHg/heartbeat. The measurement time may depend on the pulse rate of the subject 18 and the systolic blood pressure of the subject 18. In this example, the systolic blood pressure is relatively high (e.g. up to about 250 mmHg), causing the blood pressure measurement to cover a wide range of cuff pressures. For lower systolic blood pressures, the blood pressure measurement time is lower. The simulated blood pressure measurements in this example indicate a blood pressure that is far above the hypotensive range, which indicates ROSC and, consequently, successful CPR therapy. In fact, the differences between the determined systolic and diastolic blood pressures among the different predefined (baseline) pressures largely reflect the relatively rapidly rising blood pressure over time. Hence, the blood pressure measurements that are performed earliest, i.e. those that are triggered at low predefined (baseline) pressures, provide the lowest blood pressure values.

As mentioned earlier, if the diastolic blood pressure of the subject 18 is above the predefined pressure up to which the cuff 14 is inflated, the amplitude of the pressure oscillations detected inside the cuff 14 will increase as the pressure in the cuff 14 is increased over the course of the blood pressure measurement, as the maximum oscillation will be reached when the pressure in the cuff 14 is approximately equal to the MAP. This is the case in the example shown in FIG. 6, as the blood pressure has in fact increased.

Figure 7:
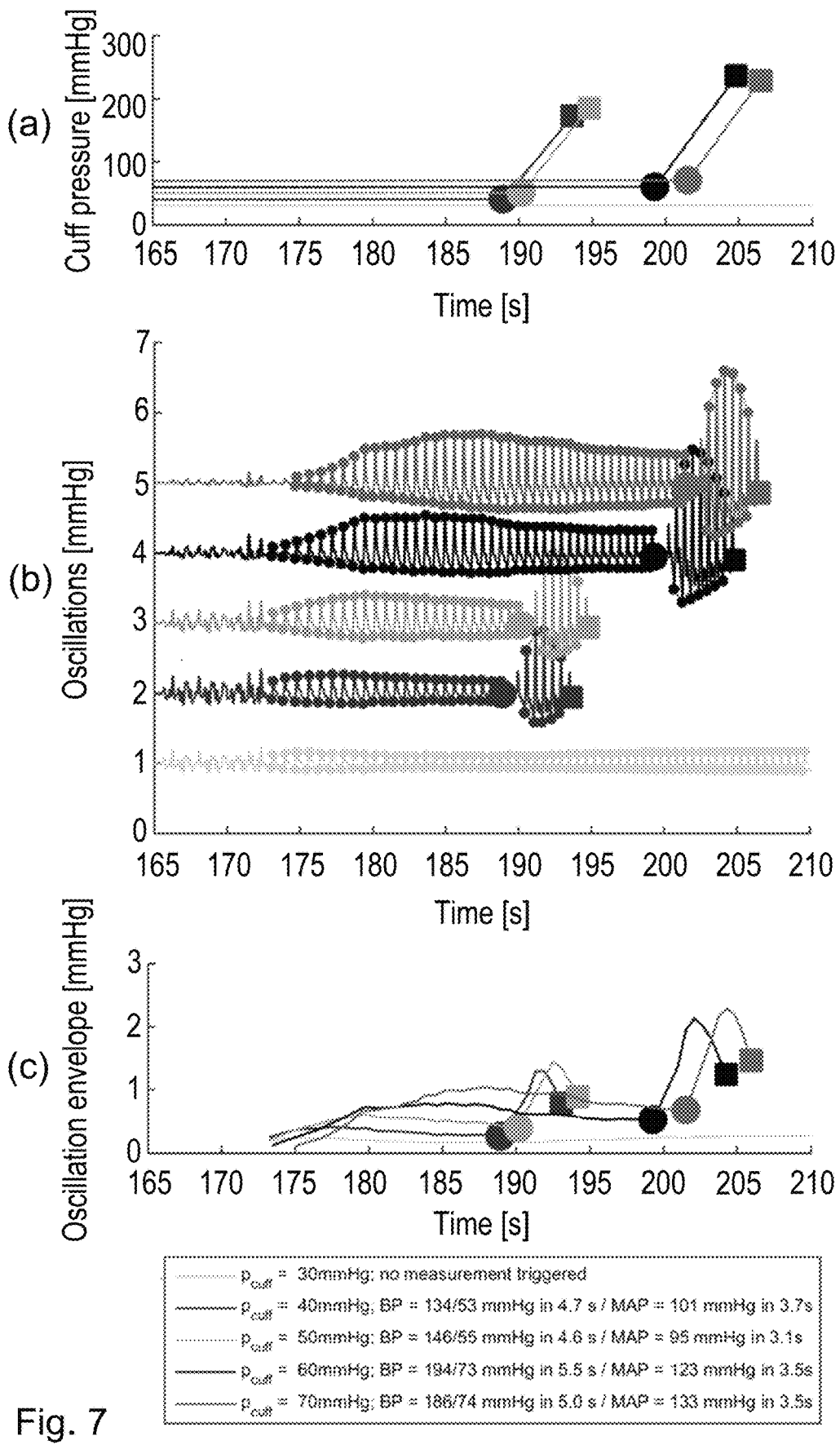
FIG. 7 is an illustration of various signals for a cuff as a function of time.
Figure 7:
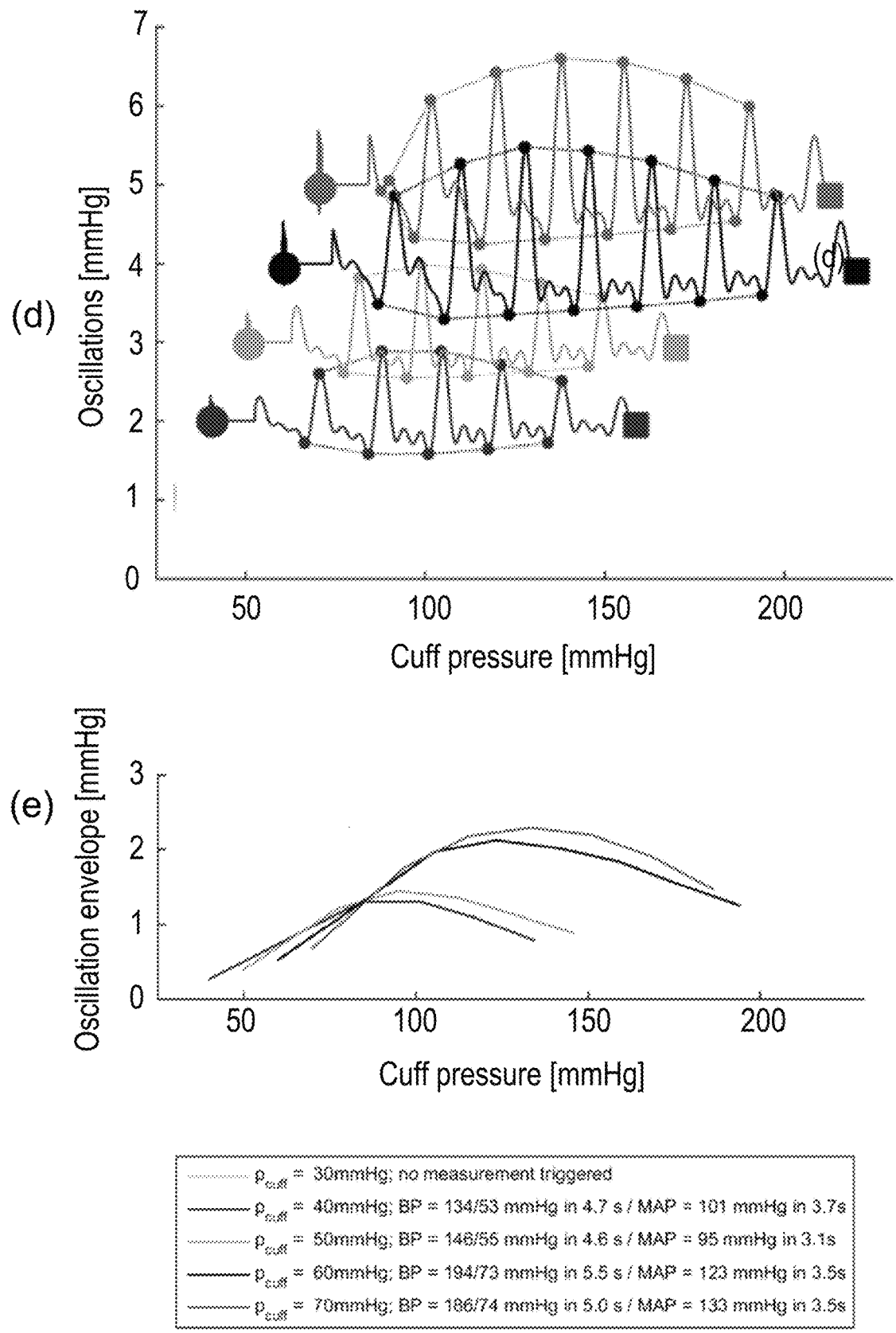

Another example of the resulting pressure signals for the cuff 14 as a function of time are illustrated in FIG. 7. FIGS. 7(a), (b), (c), (d) and (e) illustrate the same signals as FIGS. 6(a), (b), (c), (d) and (e) respectively and thus the description of FIGS. 6(a), (b), (c) (d) and (e) will be understood to also apply to FIGS. 7(a), (b), (c), (d) and (e) respectively. However, while the signals of FIGS. 6(a), (b), (c), (d) and (e) are obtained with a blood pressure measurement speed of 9 mmHg/heartbeat, the signals of FIGS. 7(a), (b), (c), (d) and (e) are obtained with a blood pressure measurement speed of 18 mmHg/heartbeat. With a blood pressure measurement speed of 18 mmHg/heartbeat as illustrated in FIG. 7 (which is doubled from the value of 9 mmHg/heartbeat as illustrated in FIG. 6), the measurement time may be reduced to approximately 5-6 seconds for estimating systolic and diastolic blood pressure and to below approximately 4 seconds for estimating MAP.

As described earlier, in some of the embodiments described herein, the processor 102 can be configured to trigger the blood pressure measurement for the subject 18 when an amplitude of the pressure oscillations detected inside the cuff 14 (e.g. substantially) decreases subsequent to reaching a maximum amplitude and, for example, it can be assumed that a diastolic blood pressure of the subject 18 has risen above the pressure inside the cuff 14 when the amplitude of the pressure oscillations detected inside the cuff 14 (e.g. substantially) decreases subsequent to reaching the maximum amplitude. However, it may be that this decrease in amplitude of the pressure oscillations actually results from a decrease in the blood pressure of the subject 18 to a value well below the pressure inside the cuff 14. This may be indicative of a serious condition, which may require an acute response by physicians instead of a regular blood pressure measurement.

Thus, in some embodiments, the processor 102 can be configured to trigger the blood pressure measurement for the subject 18 based on the pressure oscillations detected inside the cuff 14 provided that a blood pressure of the subject 18 is greater than (or has risen beyond) a pressure detected inside the cuff 14. This prevents the blood pressure measurement from being (erroneously or falsely) triggered when the blood pressure of the subject 18 falls below the pressure inside the cuff 14 instead of rising above it. In this way, by reducing the risk that a blood pressure measurement is (erroneously or falsely) triggered, the method described herein can be further improved. There may be various ways in which the processor 102 can be configured to determine whether the blood pressure of the subject 18 is greater than (or has risen beyond) the pressure inside the cuff 14.

In some embodiments, for example, the processor 102 can be configured to determine whether the blood pressure of the subject 18 is greater than (or has risen beyond) the pressure inside the cuff 14 based on a morphology of the signal indicative of the pressure oscillations detected inside the cuff 14. In particular, when the pressure inside the cuff 14 is below the blood pressure of the subject 18, blood flow is passed through the artery underneath the cuff 14, resulting in a signal indicative of the pressure oscillations detected inside the cuff 14 that peaks and subsequently returns to its minimum value gradually (or slowly) after the peak. On the other hand, when the pressure inside the cuff 14 is above the blood pressure of the subject 18, the artery is blocked, resulting in a signal indicative of the pressure oscillations detected inside the cuff 14 that peaks and subsequently returns to its minimum value suddenly (or quickly) after the peak.

This difference in signal morphology can thus be used to identify whether the blood pressure of the subject 18 is greater than (or has risen beyond) the pressure inside the cuff 14. For example, the processor 102 can be configured to determine whether the blood pressure of the subject 18 is greater than (or has risen beyond) the pressure inside the cuff 14 based on the rate at which the signal indicative of the pressure oscillations detected inside the cuff 14 returns to a minimum value subsequent to reaching a maximum value (or peak). The processor 102 can be configured to determine that the blood pressure of the subject 18 is greater than (or has risen beyond) the pressure inside the cuff 14 if this rate is less than a threshold value.

Figure 8:
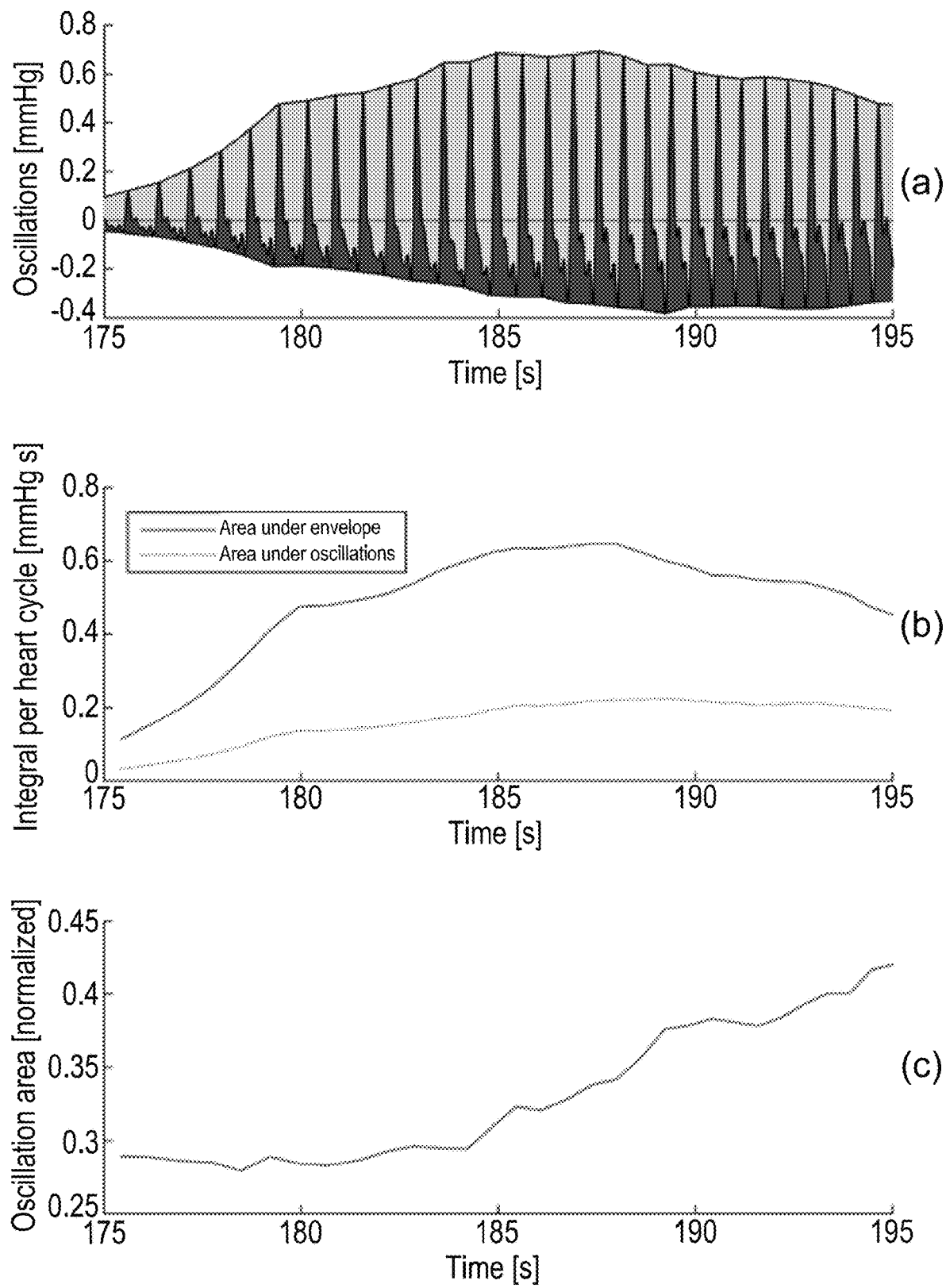
FIG. 8 is an illustration of a pressure oscillation signal, an envelope of the signal and corresponding areas for a cuff as a function of time.

FIG. 8 illustrates a pressure oscillation signal, an envelope of that signal and corresponding areas calculated for a cuff 14 as a function of time, which demonstrates an example of a manner in which the rate at which the signal indicative of the pressure oscillations detected inside the cuff 14 returns to a minimum value subsequent to reaching a maximum value (or peak) can be quantified. FIG. 8(a) illustrates the signal indicative of the pressure oscillations detected inside the cuff 14 together with the envelope of that signal. The signal indicative of the pressure oscillations detected inside the cuff 14 illustrated in FIG. 8(a) is the same as the top signal shown in FIG. 5(b) but over the limited time scale of 175-195s. The pressure inside the cuff 14 remains at a predefined pressure $P_{cuff}$ of 70 mmHg over this period. The envelope of that signal comprises an upper envelope and a lower envelope. The upper envelope is a curve or line that connects the maxima of the pressure oscillations over time. The lower envelope is a curve or line that connects the minima of the pressure oscillations over time.

In this example, the processor 102 can be configured to calculate the area between the signal indicative of the pressure oscillations detected inside the cuff 14 and the upper envelope of that signal, which is illustrated in light grey in FIG. 8(a). This area may be calculated as an integral between the signal indicative of the pressure oscillations detected inside the cuff 14 and the upper envelope of that signal per heart cycle. In this example, the processor 102 may also be configured to calculate the area between the signal indicative of the pressure oscillations detected inside the cuff 14 and the lower envelope of that signal, which is illustrated in dark grey in FIG. 8(a). This area may be calculated as an integral between the signal indicative of the pressure oscillations detected inside the cuff 14 and the lower envelope of that signal per heart cycle.

FIG. 8(b) illustrates the calculated areas as a function of time. In particular, in FIG. 8(b), the combination (i.e. sum) of (i) the area between the signal indicative of the pressure oscillations detected inside the cuff 14 and the lower envelope of that signal (which is illustrated in dark grey in FIG. 8(a)) and (ii) the area between the signal indicative of the pressure oscillations detected inside the cuff 14 and the upper envelope of that signal (which is illustrated in light grey in FIG. 8(a)) is labelled as "Area under envelope". In other words, in FIG. 8(b), the area inside or within the envelope (which is illustrated in light and dark grey in FIG. 8(a)) is labelled as "Area under envelope". Also, the area between the signal indicative of the pressure oscillations detected inside the cuff 14 and the lower envelope of that signal (which is illustrated in dark grey in FIG. 8(a)) is labelled as "Area under oscillations".

In this example, the processor 102 can also be configured to calculate the ratio of the area between the signal indicative of the pressure oscillations detected inside the cuff 14 and the lower envelope of that signal (which is illustrated in dark grey in FIG. 8(a)) to a combination (e.g. the sum) of: (i) the area between the signal indicative of the pressure oscillations detected inside the cuff 14 and the lower envelope of that signal (which is illustrated in dark grey in FIG. 8(a)), and (ii) the area between the signal indicative of the pressure oscillations detected inside the cuff 14 and the upper envelope of that signal (which is illustrated in light grey in FIG. 8(a)). In other words, the processor 102 can also be configured to calculate the ratio of the area between the signal indicative of the pressure oscillations detected inside the cuff 14 and the lower envelope of that signal (which is illustrated in dark grey in FIG. 8(a)) to the area inside or within the envelope (which is illustrated in light and dark grey in FIG. 8(a)).

FIG. 8(c) illustrates the ratio as a function of time, where the ratio is denoted as "Oscillation area". As illustrated in FIG. 4, the mean blood pressure rises from about 50 mmHg to beyond 100 mmHg, i.e. from below the pressure inside the cuff 14 to above the pressure inside the cuff 14. As a consequence, the increase in the ratio shown in FIG. 8(c) is seen. The ratio quantifies the rate at which the signal indicative of the pressure oscillations detected inside the cuff 14 returns to a minimum value subsequent to reaching a maximum value (or peak). As mentioned earlier, the processor 102 can be configured to determine that the blood pressure of the subject 18 is greater than (or has risen beyond) the pressure inside the cuff 14 if this rate is less than a threshold value.

In another example of a manner in which the rate at which the signal indicative of the pressure oscillations detected inside the cuff 14 returns to a minimum value subsequent to reaching a maximum value (or peak) can be quantified, the processor 102 can be configured to calculate a fraction of a pulse period over which the signal indicative of the pressure oscillations detected inside the cuff 14 is positive, e.g. by detecting the zero crossings in that signal.

Alternatively or in addition to the signal morphology-based method described above, in some embodiments, the processor 102 can be configured to determine whether the blood pressure of the subject 18 is greater than (or has risen beyond) the pressure inside the cuff 14 based on data acquired from at least one sensor configured to detect a pulse of the subject 18. For example, the at least one sensor may comprise a photoplethysmography (PPG) sensor. The sensor may be positioned on the subject 18 distally to the cuff 14 (e.g. with the cuff 14 around the upper arm of the subject 18 and the sensor positioned on a finger on the same arm of the subject 18). When the pressure inside the cuff 14 exceeds the blood pressure of the subject 18, the sensor detects no pulse as the cuff 14 blocks all blood flow to the sensor. On the other hand, when the sensor detects a pulse, blood flow is reaching the sensor, which can only occur if the blood pressure exceeds the cuff pressure. Thus, in these embodiments, the processor 102 can be configured to determine that the blood pressure of the subject 18 is greater than (or has risen beyond) the pressure inside the cuff 14 if the data acquired from the at least one sensor is indicative of a detected pulse.

The apparatus described herein may be used alone or in combination with other apparatus. For example, the apparatus described herein may be used in combination with one or more sensors (such as one or more PPG sensors), which are more robust from any motions of the measurement site 20 of the subject 18. The one or more sensors may, for example, be positioned on the body of the subject 18 (e.g. at different body locations) and provide information about the pulse rate when a spontaneous pulse has returned.

There is also described a computer program product comprising a computer readable medium. The computer readable medium has a computer readable code embodied therein. The computer readable code is configured such that, on execution by a suitable computer or processor (such as the processor 102 of the apparatus 12), the computer or processor is caused to perform the method described herein. The computer readable medium may be, for example, any entity or device capable of carrying the computer program product.

For example, the computer readable medium may include a data storage, such as a ROM (such as a CD-ROM or a semiconductor ROM) or a magnetic recording medium (such as a hard disk). Furthermore, the computer readable medium may be a transmissible carrier, such as an electric or optical signal, which may be conveyed via electric or optical cable or by radio or other means. When the computer program product is embodied in such a signal, the computer readable medium may be constituted by such a cable or other device or means. Alternatively, the computer readable medium may be an integrated circuit in which the computer program product is embedded, the integrated circuit being adapted to perform, or used in the performance of, the method described herein.

Therefore, there is described herein an apparatus 12, a system 10, a method 200 and a computer program product that address the limitations associated with the existing techniques. An improved apparatus 12, system 10, method 200 and computer program product for use in measuring blood pressure is thus described.

Variations to the disclosed embodiments can be understood and effected by those skilled in the art in practicing the principles and techniques described herein, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored or distributed on a suitable medium, such as an optical storage medium or a solid-state medium supplied together with or as part of other hardware, but may also be distributed in other forms, such as via the Internet or other wired or wireless telecommunication sys-

The invention claimed is:

1. An apparatus for use in measuring blood pressure, the apparatus comprising a processor configured to:
   acquire a signal indicative of pressure oscillations detected inside a cuff inflated to pressurize a measurement site of a subject undergoing cardiopulmonary resuscitation, wherein the pressure oscillations detected inside the cuff are indicative of a pulse of the subject; and
   trigger a blood pressure measurement for the subject based on the pressure oscillations detected inside the cuff;
   wherein the processor is configured to:
   trigger the blood pressure measurement for the subject when an amplitude of the pressure oscillations detected inside the cuff decreases subsequent to reaching a maximum amplitude.

2. The apparatus as claimed in claim 1, wherein the processor is configured to:
   trigger the blood pressure measurement for the subject when the amplitude of the pressure oscillations detected inside the cuff decreases to a predefined fraction of the maximum amplitude.

3. The apparatus as claimed in claim 2, wherein the predefined fraction of the maximum amplitude is a fraction that is less than or equal to three quarters of the maximum amplitude.

4. The apparatus as claimed in claim 1, wherein the processor is configured to set a predefined pressure to which the cuff is to be inflated, wherein the predefined pressure is a pressure in a range from 30 to 70 mmHg.

5. The apparatus as claimed in claim 1, wherein the processor is configured to adjust a speed with which the cuff is inflated based on the pulse rate of the subject determined from the pressure oscillations detected inside the cuff indicative of the pulse of the subject.

6. The apparatus as claimed in claim 1, wherein the processor is configured to:
   if an amplitude of the pressure oscillations decreases to a fraction of a predefined fraction of a maximum amplitude, stop the blood pressure measurement and/or output an instruction to restart cardiopulmonary resuscitation.

7. The apparatus as claimed in claim 1, wherein the processor is configured to:
   suppress at least one harmonic in the signal indicative of pressure oscillations detected inside the cuff, wherein the at least one harmonic corresponds to a frequency of a compression used in the cardiopulmonary resuscitation.

8. The apparatus as claimed in claim 1, wherein the processor is configured to:
   acquire one or more signals indicative of compression applied to the subject;
   detect when compressions applied to the subject during the cardiopulmonary resuscitation cease; and
   trigger the blood pressure measurement for the subject when the compressions are detected to cease.

9. The apparatus as claimed in claim 1, wherein the processor is configured to:
   trigger the blood pressure measurement for the subject based on a rate at which the signal indicative of the pressure oscillations detected inside the cuff returns to a minimum value subsequent to reaching a maximum value.

10. The apparatus as claimed in claim 1, wherein the processor is configured to:
    trigger the blood pressure measurement for the subject based on the rate at which the signal indicative of the pressure oscillations detected inside the cuff returns to the minimum value subsequent to reaching the maximum value being less than a threshold value.

11. The apparatus as claimed in claim 1, wherein the processor is configured to:
    acquire a plurality of signals indicative of pressure oscillations detected inside a respective plurality of cuffs inflated to pressurize different measurement sites of the subject; and
    trigger the blood pressure measurement for the subject based on the pressure oscillations detected inside the plurality of cuffs.

12. A system for use in measuring blood pressure, the system comprising:
    an apparatus for use in measuring blood pressure according to claim 1; and
    one or more wearable cuffs.

13. The system as claimed in claim 12, wherein the processor is configured to:
    trigger the blood pressure measurement for the subject while a cuff of the one or more wearable cuffs is maintained at a constant pressure.

14. A method for use in measuring blood pressure, the method comprising:
    acquiring via an apparatus a signal indicative of pressure oscillations detected inside a cuff inflated to pressurize a measurement site of a subject undergoing cardiopulmonary resuscitation, wherein the pressure oscillations detected inside the cuff are indicative of a pulse of the subject; and
    triggering by the apparatus a blood pressure measurement for the subject based on the pressure oscillations detected inside the cuff;
    wherein the blood pressure measurement is triggered for the subject when an amplitude of the pressure oscillations detected inside the cuff decreases subsequent to reaching a maximum amplitude.

15. A non-transitory computer readable medium, the computer readable medium having a computer readable code embodied therein, the computer readable code being configured such that, on execution by a suitable computer or processor, the computer or processor is caused to perform the method comprising:
    acquiring a signal indicative of pressure oscillations detected inside a cuff inflated to pressurize a measurement site of a subject undergoing cardiopulmonary resuscitation, wherein the pressure oscillations detected inside the cuff are indicative of a pulse of the subject; and
    triggering a blood pressure measurement for the subject based on the pressure oscillations detected inside the cuff;
    wherein the blood pressure measurement is triggered for the subject when an amplitude of the pressure oscillations detected inside the cuff decreases subsequent to reaching a maximum amplitude.

* * * * *